United States Patent [19]

George

[11] 3,981,594
[45] Sept. 21, 1976

[54] OPTICAL ABSORPTION CELL WITH MAGNETIC STIRRING

[75] Inventor: Kenyon Palmer George, Los Altos, Calif.

[73] Assignee: Varian Associates, Palo Alto, Calif.

[22] Filed: Oct. 1, 1975

[21] Appl. No.: 618,410

[52] U.S. Cl. ............................... 356/246; 250/576; 356/197; 356/201
[51] Int. Cl.² .......................................... G01N 1/00
[58] Field of Search ........... 356/181, 197, 201, 208, 356/246; 250/573, 576; 259/DIG. 46

[56] References Cited
UNITED STATES PATENTS

| | | | |
|---|---|---|---|
| 3,526,462 | 9/1970 | McCurdy et al. | 356/246 |
| 3,545,864 | 12/1970 | Dibbern | 356/246 |

*Primary Examiner*—John K. Corbin
*Assistant Examiner*—Matthew W. Koren

[57] ABSTRACT

An optical absorption cell enabling improved magnetic stirring of the cell contents. The cell includes an oblong container for fluidic samples to be subjected to optical absorption analysis. A magnetic stirrer body is provided at the bottom of the container, which body is rotatable in response to an externally applied rotating magnetic field to effect agitation of the sample. Partitioning means are mounted in the container in non-interfering relationship to the light projection path through the container. The partitioning means cooperate with the stirrer body to define an upward flow path adjacent to the walls of the container, and a downward flow path toward the interior of the container. The partitioning means extend at least to a level in the sample above the light path, whereby relatively complete agitation of the fluid sample is effected, including agitation within portions of the sample body residing within the projected light path.

6 Claims, 7 Drawing Figures

U.S. Patent  Sept. 21, 1976  3,981,594
FIG.1 *PRIOR ART*
FIG.2 *PRIOR ART*
FIG. 3
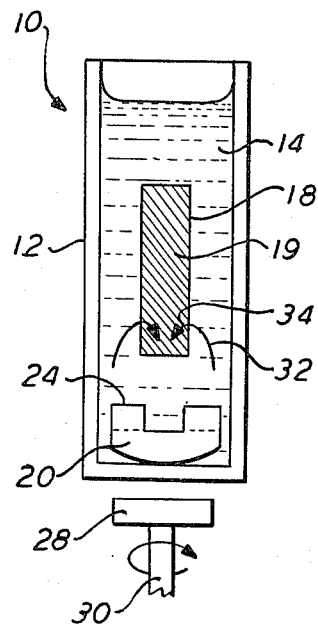
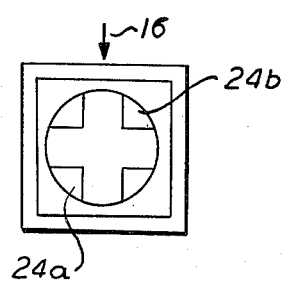
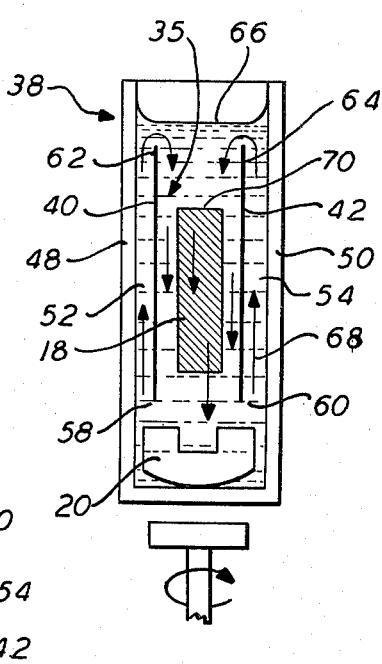
FIG.4
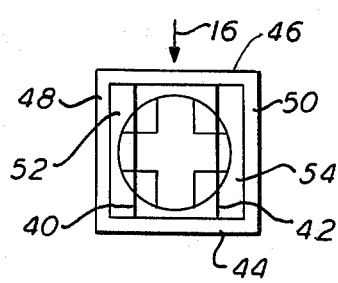
FIG.5
FIG.6
FIG.7
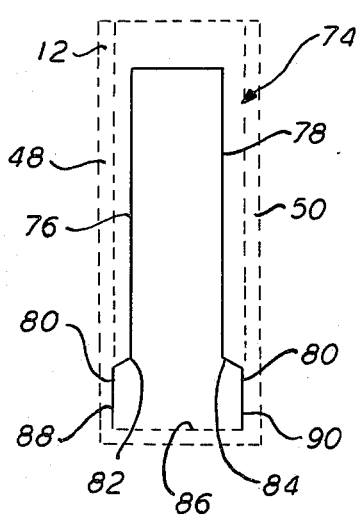
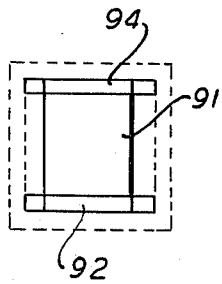
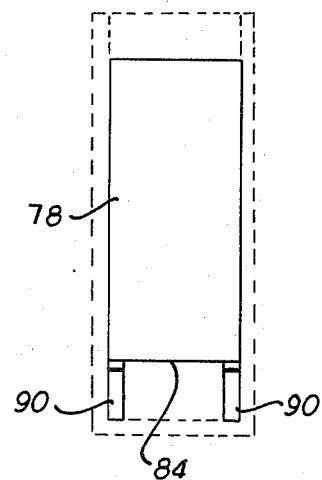

OPTICAL ABSORPTION CELL WITH MAGNETIC STIRRING

BACKGROUND OF INVENTION

This invention relates generally to optical absorption spectroscopy, and more specifically relates to the optical absorption cells utilized in such environments for containing the samples which are subjected to analysis.

In the practice of optical absorption spectroscopy, apparatus such as spectrophotometers are utilized, which include one or more optical paths in which sample or reference materials are inserted, in order that the light absorption characteristics of the materials may be evaluated. The materials to be thus analyzed are physically contained in an optical absorption cell, which typically comprises a small rectangular container, the opposed sides of which are relatively transparent to the wavelengths being utilized during analysis.

Depending upon the nature of the sample being analyzed it is frequently required that agitation be provided within the absorption cell, in order to maintain a high degree of uniformity. A common arrangement that has been utilized in the past to enable such result, incorporates so-called magnetic stirrers. According to this well-known arrangement, a magnetically responsive agitator is positioned at the bottom of the cell container and is caused to rotate in synchronism with a rotating magnetic field provided beneath the cell, e.g. by a rotating bar magnet.

The dimensions of many typical optical absorption cells are such that the cell is relatively oblong, e.g. the cell container may typically have a height of 4 to 5 centimeters, and a transverse cross-section of perhaps 1 centimeter by 1 centimeter. Particularly in configurations of this type, magnetic stirrers of the aforementioned type are relatively ineffective in providing good mixing. This type of problem is especially significant where the liquid present in the cell is of relatively high viscosity, or if it is required (in accordance with the material being analyzed) to maintain heavy particles suspended in the liquid. Under the type of conditions cited, the stirring tends to occur only in the lower one-third to one-half of the cell, whereas the upper one-half to two-thirds of the cell may remain in good part, undisturbed.

In accordance with the foregoing it may be regarded as an object of the present invention, to provide an improved optical absorption cell, wherein magnetic stirring is effective to provide excellent and relatively complete intermixing of the fluids contained within such cell, including excellent agitation of such materials as may be suspended within such fluid.

It is a further object of the invention to provide an optical absorption cell utilizing magnetic stirring, wherein excellent agitation of the cell contents is assured throughout the entire volume of such cell, even when such cell is of a relatively elongated configuration.

SUMMARY OF THE INVENTION

Now in accordance with the present invention, the foregoing objects, and others as will become apparent in the course of the ensuing specification, are achieved in an optical absorption cell of the type including a container for fluidic samples which are to be subjected to optical absorption analysis, and a magnetic stirrer body at the bottom of the container, which body is rotatable in response to an externally applied rotating magnetic field to effect agitation of the sample. In accordance with the principles of the invention, partitioning means are mounted in the container, in non-interfering relationship to the light projection path through the container. The partitioning means serve in cooperation with the rotating stirrer body, to define an upward flow space adjacent to the walls of the container, and a downward flow space toward the interior of the container. The partitioning means extends at least to an upper level in the sample, which is above the light projection path through same; hence relatively complete agitation of the fluid example is effected, at least in all portions of the sample residing within the path of light projection.

In a typical instance where the sample container is of rectangular cross-section and elongated in height, the partitioning means may take the form of a pair of generally planar partitions extending across the cell in a direction parallel to that of light passage. The partitions are spaced to alternate sides of the light projection path, so as not to impede same, and the sides of the partitions opposed to the light projection path are spaced from the adjacent container walls to define the upward flow space for the fluidic sample. The bottom of these partitions are above the stirring body, and the tops of the partitions are beneath the sample surface level. Accordingly rotation of the stirring body drives the fluidic sample in an outward direction — so that it passes beneath the said partitions, upwardly through the flow space between the partitions and adjacent walls, thence across the top of the partitions, and thence downwardly through the center of the cell and back to the stirring body.

The partitions in a preferred embodiment, may be supported by means of outwardly bowed legs at the bottom of the partitions, with the bottom of these legs residing against the walls of the container. Crosspieces are also provided between the tops of the partitions, and in consequence of this arrangement the spacing of the partitions is accurately maintained. The partitions, legs and crosspieces may be formed of one continuous stamping of sheet metal, thereby comprising an easily removeable, unitized insert for the cell container.

BRIEF DESCRIPTION OF DRAWINGS

The invention is diagrammatically illustrated by way of example, in the drawings appended hereto, in which:

FIG. 1 is a longitudinal cross-section, somewhat schematic in nature, illustrating a prior art optical absorption cell including magnetic stirring features;

FIG. 2 is a top plan view of the FIG. 1 device;

FIG. 3 is a longitudinal cross-section, somewhat schematic in nature, through an optical absorption cell incorporating the basic features of the present invention;

FIG. 4 is a top plan view of the FIG. 3 device;

FIG. 5 is an elevational end view of a unitized insert, embodying partitioning means in accordance with the invention;

FIG. 6 is a top plan view of the FIG. 5 insert; and FIG. 7 is a side elevational view of the insert of FIGS. 5 and 6.

DESCRIPTION OF PREFERRED EMBODIMENT

In FIGS. 1 and 2 an optical absorption cell 10 is depicted, which is substantially a prior art device. The depiction is being set forth, in order to clearly illustrate the deficiencies of the prior art, to which the present invention is addressed. Cell 10 comprises a sample container 12, which as best seen in the top plan view of FIG. 2, is of generally rectangular cross-section. Cell 10 is elongated in the direction of its height; it may thus typically have a cross-section of the order of 1 × 1 centimeters, and a height of the order of 4 to 5 centimeters. The container 12 comprises a material which is relatively transparent to the wavelengths of the analyzing radiation which is utilized during an optical absorption test of a sample 14 which is held within container 12.

It should, of course, be understood in connection with the foregoing discussion, that the term "sample" as used herein merely designates the material held within container 12. Depending upon the specific type of absorption spectroscopy system being utilized, this "sample" may be present in other than the "sample path" of the instrument. In particular, in certain types of dual beam operation, the optical absorption cell of the invention may be mounted additionally or alternatively in the "reference path" portion of the apparatus.

For purposes of the diagrammatic depiction of FIGS. 1 and 2, it may be assumed that the analyzing radiation (i.e. "light") is incident upon cell 10 in the direction indicated by arrow 16. It, of course, will be understood in accordance with the usual terminology pertinent to the present art, that the term "light" includes such portions of the electromagnetic spectrum as are customarily utilized in absorption spectroscopy. The term may thus include wavelengths such as those of the ultra-violet and infrared portions of the spectrum, which, while generally regarded as "optical" are not "visible" in the sense of being detectable by the unaided human eye.

It may be further assumed for purposes of analysis herein, that the analyzing light in its passage through cell 12 and the contained sample 14, defines a light projection path 18, the boundaries of which are indicated by cross-sectioning 19.

In accordance with prior techniques utilized in this art, a magnetic stirring body 20 is positioned at the bottom of container 12. Body 20 is of circular configuration with respect to a section transverse to its axis of rotation, and is defined at its under portion by an arcuate base 22. Similarly, the upper side of stirring body 20, may include a series of projections 24 toward the circumference of the body, which projections interact with and agitate the sample 14 during rotation of body 20.

Stirring body 20 carries magnetic poles towards diametrically opposed portions thereof. For example, opposed projections such as 24a and 24b may be of opposite magnetic polarity. By rotating a magnetic means such as the bar magnet 28 shown beneath the container 12, a rotating magnetic field is established in the vicinity of stirring body 20 (assuming the container 12 is substantially non-magnetic), causing the stirring body 24 to follow the rotation of the said field, and thus become an agitator for the fluidic sample 14. Rotation of bar magnet 28 may be effected via a shaft 30, which can be powered by any convenient means as, for example, by an electric motor.

The sample 14 may be regarded as generally fluid in character. Such sample may comprise a pure liquid; or may comprise a liquid carrier in which are suspended particles of a composition which is to be analyzed. In any event, the liquid component of the fluidic sample may be of varying viscous characteristics; and if the viscosity of such liquid is relatively high, it will be evident that the agitation provided by stirring means 20 may be of relatively limited efficacy.

Thus referring to FIG. 1, it is seen that as the stirring body 20 rotates, the fluidic sample 14 in contact therewith, is driven in a radially outward direction — due to centrifugal forces — and upon striking the inner walls of container 12 flows generally upward along such walls. This phenomena is indicated by the arrows 32, which also render clear that — depending upon the speed of agitation and particularly upon the viscosity characteristics of sample 14 — the degree of upward movement of the flowing sample may be sharply restricted. In consequence the flow lines for the sample may typically bend around, as at 34, and begin their return toward the stirrer body at a point in container 12 which is relatively close to the bottom thereof. Indeed with very viscous samples, and at typical agitation rates, a good portion of the sample body, including especially portions within the light projection path 18, may be subjected to little or no agitation. In consequence, the analyzing light 16 may pass through portions of the sample which are quite unrepresentative of the material intended to be analyzed.

In FIGS. 3 and 4, views generally corresponding to those of FIGS. 1 and 2 appear. In these instances, however, the optical absorption cell 38, includes the features of the present invention. It will thus be noted in these latter Figures, that similar portions of the drawings are identified in correspondence to the identical elements appearing in FIGS. 1 and 2. The cell 38, however, now is found to include a partitioning means 35, which in the embodiment here shown, takes the form of a pair of planar partitions, 40 and 42.

The partitions 40 and 42 are parallel to one another, and extend across container 12 between the walls 44 and 46 which are transverse to the analyzing light 16. The substantially planar partitions 40 and 42 are therefore approximately parallel to the direction of the light projection path 18. The partitions are further, so spaced with respect to one another, as to be on alternate sides of the light path 18, and thus to present no impediment to passage of same.

Each partition 40 and 42, is further, spaced from the lateral wall 48 and 50 adjacent to same, so as to thereby define a pair of upward flow spaces 52 and 54. The bottom edges 58 and 60 of each partition is also spaced from the uppermost portions of stirrer body 20, so that the fluidic sample 14 upon agitation by body 20, is free to pass upwardly through the spaces 52 and 54. Further, it will be noted that the top edges 62 and 64 of each partition, are beneath the position of sample surface 66. In consequence of the arrangement set forth, the flow for fluidic sample 14 is now constrained to follow the pattern indicated by arrows 68, according to which the sample passes upwardly through spaces 52 and 54 under the impetus of the centrifugal acceleration provided by rotating body 20; thence passes over the top edges 62 and 64 of the partitions; and then flows downwardly through the center of the sample and back to the body 20.

The top edges 62 and 64 of the partitions are seen to be well above the topmost portion 70 of the light path 18, in consequence of which it will be clear that the agitated flow pattern described, occurs throughout the entire volume of the sample which is traversed by the said light beam.

The depictions of FIGS. 3 and 4 with respect to the partitioning means 35 is diagrammatic in nature; and accordingly the support elements for the partitions 40 and 42 are not explicitly shown herein. These may, however, constitute any convenient frame support, series of legs or the like.

In FIGS. 5 through 7 a preferred embodiment of partitioning means 35 is set forth. The device there shown comprises a unitized insert 74, which is readily insertible and removeable from the container 12, so as to permit ready access to the container for filling, servicing, or so forth. Insert 74 may be stamped from a single piece of sheet metal. Alternatively, in applications where resistance to chemical activity is of particular importance, insert 74 may be fabricated from other kinds of rigid material such as plastic or plastic coated metal. Insert 74 includes a pair of flat portions 76 and 78 — which correspond to the partitions 40 and 42 of FIGS. 3 and 4. At the lower lateral edge of each portion 76 and 78, a leg 80 is bowed outwardly therefrom. Legs 80 extend beneath the bottom edges 82 and 84 of portions 76 and 78, and support insert 74 upon the bottom 86 of container 12. The bowed legs 80 include flattened lateral portions 88 and 90, which rest against the interior of walls 48 and 50. As seen in FIG. 6, the top of insert 74 is generally open at 91; however, crosspieces 92 and 94 extend between the top edges of portions 76 and 78, thus rendering the entire insert 74 a relatively rigid structure. In consequence, with the flattened portions 88 and 90 of the legs in contact with walls 48 and 50, the spacing between portions 76 and 78 and the adjacent walls is maintained in relatively accurate fashion.

While the present invention has been particularly set forth in terms of specific embodiments thereof, it will be understood in view of the present disclosure, that numerous variations upon the invention are now enabled to those skilled in the art, which variations yet reside within the scope of the present teaching. Accordingly the invention is to be broadly construed, and limited only by the scope and spirit of the claims now appended hereto.

I claim:

1. An optical absorption cell for use in optical absorption spectroscopy, comprising:
   a container for fluidic samples to be subjected to optical absorption;
   a magnetic stirrer body at the bottom of said container, said body being rotatable in response to an externally applied rotating magnetic field, for effecting agitation of said sample; and
   partitioning means mounted in said container in non-interfering relationship to the anticipated light projection path through said container; said partitioning means defining in cooperation with the rotation of said stirrer body an upward flow space adjacent the walls of said container, and a downward flow space toward the interior of said container; said partitioning means extending at least to a level in said sample above the said light projection, whereby relatively complete agitation of said fluidic sample is effected at least in the portions of said sample residing within said light projection path.

2. Apparatus in accordance with claim 1, wherein said container is of generally rectangular cross-section; and wherein said partitioning means comprises at least a pair of generally planar partitions extending across said container in a direction parallel to that of said light path, said partitions being spaced to alternate sides of said light path, the sides of said partitions opposed to said light path being spaced from the adjacent walls of said container to define said upward flow space; and the space between said partitions defining said downward flow space; the bottom of said partitions being above said stirring body to enable fluid flow into said upward flow space, and the top of said partitions being beneath said anticipated sample surface level, to enable flow to said downward flow space.

3. Apparatus in accordance with claim 2, wherein said planar partitions are supported by legs extending downwardly from the bottom of said partition, at least a pair of crosspieces extending between the top edges of said partitions, and said legs being bowed outwardly to reside against the interior walls of said container, thereby in cooperation with said crospeices maintaining the spacing of said partitions with respect to said adjacent walls.

4. Apparatus in accordance with claim 3, wherein said partitioning means comprises a unitized insert, removeable and insertible from said container.

5. Apparatus in accordance with claim 2, wherein said cell is oblong.

6. An optical absorption cell enabling improved magnetic stirring of the cell contents, comprising:
   an oblong container for fluidic samples to be subjected to analysis, said container including at least two opposed parallel sides for transmission through said cell of an analyzing light beam;
   a magnetic stirring body at the bottom end of said container, said body being rotatable by an externally applied magnetic field to effect agitation of said fluid sample; and
   at least a pair of partitions extending across said cell in a direction parallel to that of said light beam passage; said partitions being spaced to alternate sides of the light path through said cell, whereby not to impede said light; the sides of said partitions non-adjacent said light both being spaced from the adjacent walls of said container; the bottom of said partitions being above said stirring body and the top of said partitions being beneath said anticipated sample level, whereby rotation of said stirring body causes fluid flow in an upward direction through said spaces between said partitions and said adjacent walls, and a return flow downwardly through the space between said partitions, thereby to effect relatively complete agitation of said fluid.

* * * * *